US008900576B2

(12) United States Patent
Vaccaro et al.

(10) Patent No.: US 8,900,576 B2
(45) Date of Patent: Dec. 2, 2014

(54) PHARMACEUTICAL COMPOSITIONS CONTAINING HYALURONIC ACID AND COLLAGENASE FOR THE TOPICAL TREATMENT OF WOUNDS, BURNS AND ULCERS

(75) Inventors: Susanna Vaccaro, Abano Terme-Padova (IT); Giovanni Gennari, Abano Terme-Padova (IT); Lanfranco Callegaro, Abano Terme-Padova (IT); Antonio Giannelli, Abano Terme-Padova (IT); Salvatore Caruso, Abano Terme-Padova (IT)

(73) Assignee: Fidia Farmaceutici S.p.A, Padua (IT)

( * ) Notice: Subject to any disclaimer, the term of this patent is extended or adjusted under 35 U.S.C. 154(b) by 1345 days.

(21) Appl. No.: 11/921,835

(22) PCT Filed: Jul. 5, 2006

(86) PCT No.: PCT/EP2006/006616
§ 371 (c)(1),
(2), (4) Date: Dec. 27, 2007

(87) PCT Pub. No.: WO2007/006484
PCT Pub. Date: Jan. 18, 2007

(65) Prior Publication Data
US 2008/0206228 A1 Aug. 28, 2008

(30) Foreign Application Priority Data

Jul. 7, 2005 (IT) .......................... PD2005A000207

(51) Int. Cl.
| *A61K 38/48* | (2006.01) |
| *A61K 47/10* | (2006.01) |
| *A61K 47/06* | (2006.01) |
| *A61K 47/44* | (2006.01) |
| *A61K 47/26* | (2006.01) |
| *A61K 31/728* | (2006.01) |
| *A61K 47/36* | (2006.01) |

(52) U.S. Cl.
CPC ............. *A61K 38/4886* (2013.01); *A61K 47/10* (2013.01); *A61K 47/06* (2013.01); *A61K 47/44* (2013.01); *A61K 47/26* (2013.01); *A61K 31/728* (2013.01); *A61K 47/36* (2013.01)
USPC .......................... 424/94.67; 435/101; 536/55.2

(58) Field of Classification Search
None
See application file for complete search history.

(56) References Cited

U.S. PATENT DOCUMENTS

| 4,174,389 | A |   | 11/1979 | Cope |
| 4,732,758 | A | * | 3/1988 | Hurion et al. ................. 424/94.2 |
| 5,336,767 | A | * | 8/1994 | della Valle et al. ........... 536/55.1 |
| 5,422,103 | A |   | 6/1995 | Stern et al. |
| 6,086,872 | A |   | 7/2000 | Wegman |
| 6,120,751 | A | * | 9/2000 | Unger ........................... 424/9.51 |
| 6,468,551 | B1 | * | 10/2002 | Diec et al. ..................... 424/401 |
| 6,699,471 | B2 | * | 3/2004 | Radice et al. ................. 424/93.7 |
| 2002/0076810 | A1 |   | 6/2002 | Radice et al. |
| 2006/0122147 | A1 |   | 6/2006 | Wohlrab |

FOREIGN PATENT DOCUMENTS

| EP | 0637450 |   | 8/1993 |   |
| EP | 0852144 |   | 7/1998 |   |
| EP | 1433845 | * | 6/2004 | ............... C12N 9/52 |
| JP | 2002020279 | * | 1/2002 | ........... A61K 31/728 |
| WO | WO 9424273 |   | 10/1994 |   |
| WO | WO 0100190 |   | 1/2001 |   |

OTHER PUBLICATIONS

Machine Translation of JP 2002020279 and English abstract, Egami F, Jan. 2002, pp. 1-4.*
English abstract of JP 2002020279, Egami F, Jan. 2002, pp. 1-2.*
Weindl et al. "Hyaluronic Acid in the Treatment and Prevention of Skin Diseases: Molecular Biological, Pharmaceutical and Clincial Aspects." (2004) Skin Pharmacology and Physiology, vol. 17: 207-213.*
Lark et al. "Production and Purification of Prostromelysin and Procollagenase from IL-1 Beta-Stimulated Human Gingival Fibroblasts" (1990), Connective Tissue Research: vol. 25: 49-65.*
Rafanelli, A. et al., "Clinical Study of hyaluronic acid activity in ulcerations of the lower extemities", Chronica Dermatologica, 1986, vol. 17, No. 2, pp. 251-258.

* cited by examiner

*Primary Examiner* — Jon P Weber
*Assistant Examiner* — Teresa E Knight
(74) *Attorney, Agent, or Firm* — Birch, Stewart, Kolasch & Birch, LLP (57) ABSTRACT

The present invention concerns new compositions containing hyaluronic acid or the derivatives thereof in association with the proteolytic enzyme collagenase (and relative pharmaceutical formulations) for the preparation of a dressing for topical treatment of various kinds of wounds, burns of varying depth, pressure sores, vascular ulcers and diabetic foot ulcers as well as for the treatment of hypertrophic and keloid scars.

8 Claims, 3 Drawing Sheets

PHARMACEUTICAL COMPOSITIONS CONTAINING HYALURONIC ACID AND COLLAGENASE FOR THE TOPICAL TREATMENT OF WOUNDS, BURNS AND ULCERS

SUBJECT OF THE INVENTION

The present invention concerns new compositions containing hyaluronic acid or the derivatives thereof in association with the proteolytic enzyme collagenase (and relative pharmaceutical formulations) for the preparation of a dressing for topical treatment of various kinds of wounds, burns of varying depth, pressure sores, vascular ulcers and diabetic foot ulcers as well as for the treatment of hypertrophic and keloid scars.

BACKGROUND OF THE INVENTION

Enzymatic debridement of necrotic tissue involves the removal of such tissue by means of the action of non-toxic enzymes that are able to degrade denaturated collagen, fibrin and elastin present in the devitalised tissue, preserving the viable tissue.

This technique is preferable to mechanical/surgical debridement because it is more selective towards granulation tissue and is especially suitable in non-infected lesions such as skin ulcers of diverse etiology and of varying depth.

The enzymatic formulations available on the market today contain the proteolytic enzyme collagenase (Noruxol® and Iruxol®) or are constituted by an association of fibrinolysin and desoxyribonuclease (Elase®), all of which are effective (albeit with different results) in removing necrotic tissue, purulent exudate and fibrin (Mekkes J. R., Arch Dermatol Rese, 1998, 290:152-157).

Of great interest from the point of view of application are collagenases produced from bacteria of the *Clostridium* species, although collagenase produced from *Vibrio Alginolyticus* (*Achromobacter* collagenase EC 3.4.24.08; Borivoj k., Matrix Supplement, 1992, 1: 127-133; EP0115974 B1) produced from a non-pathogenic strain with a specific activity that is markedly superior to that of the enzyme produced from *Clostridium*, has been widely described and characterised (albeit not yet marketed).

Collagenase is a protein that is very unstable in aqueous solutions even at low temperatures. Moreover, it can easily be denaturated by chelating agents and various metal ions that can interact with the calcium ion that is essential for the enzymatic activity of the molecule.

It is an enzyme that is extremely sensitive to chemical-physical procedures such as freezing, thawing, freeze-drying and drying, processes that are often necessary in the course of preparing final pharmaceutical formulations. Various different formulations have therefore been tested to find a final composition that contains a stable, and therefore active, collagenase (EP0543521B1, patent application WO96/41870, WO93/00807, WO94/24273).

Albeit still at an experimental stage, the enzyme is used in injectable form to treat Dupuytren's contracture, a deforming condition of the fingers, while the use of collagenase is particularly important in reducing glaucoma, a disorder that causes excessive pressure in the eye with possible damage to the optic nerve, linked with an abnormal deposit of collagen within the duct that drains biological fluids from the anterior chamber of the eye.

The collagenase enzyme is mainly indicated in débridement of burns of varying depth, pressure sores, vascular ulcers and diabetic foot ulcers. Moreover, it is used to treat hypertrophic and keloid scars.

Proper wound healing requires a proper reepithelialisation phase, which follows the phase involving removing the eschar, possibly by surgical and/or enzymatic débridement. Collagen is the chief component of necrotic tissue and, consequently, it is fundamentally important to remove it in order to favour reepithelialisation of the wound. However, in the course of this operation it is necessary to protect the surrounding skin to avoid painful irritative phenomena resulting from the use of collagenase, as the enzyme is capable of degrading both denaturated and natural collagen, hydrolysing the peptide bonds of the amino acid chain. During enzymatic débridement the wound area being treated does not decrease in size, it may even increase. Therefore, when the eschar has been removed, the newly-forming granulation tissue is exposed and consequently open to dangerous bacterial infections that may jeopardise complete healing of the lesion.

The wound healing process is a complex phenomenon involving many types of cellular and humoral factors, and many phases that can favour the formation of pathological scarring, such as hypertrophic and keloid scars.

Proper healing therefore requires the application of drugs to guide (and accelerate) the wound healing process.

Scientific and patent literature contains ample descriptions and claims naming hyaluronic acid (HA) as the chief factor in the tissue regeneration processes (European patent application EP1196179).

Indeed, thanks to its special chemical-physical and biological features, hyaluronic acid participates in and modulates all the main sequential phases of wound healing:
inflammation;
formation of granulation tissue;
reepithelialisation;
scar remodelling.

Owing to its chemical-physical properties, said polysaccharide controls tissue hydration, creating the correct microclimate necessary to fast healing; moreover, its high viscosity protects the wound from possible bacterial and/or viral infections.

Thanks to its biological properties, hyaluronic acid has proved effective in protecting against free radicals, in controlling inflammatory processes and stimulating angiogenesis. Its role in controlling the expression of cytokines and trophic factors has been demonstrated, and in stabilising the granulation tissue by favouring and regulating the flow of fibroblasts and endothelial cells into the wound during reepithelialisation.

Lastly, experimental data have demonstrated an involvement of hyaluronic acid in controlling keratinocyte proliferation and the deposit of collagen in the wound, thus reducing the formation of fibrotic tissue and, therefore, of pathological scarring (John Chen W. Y. et al., Wound Repair and Regeneration, 1999, 7:79-89).

HA is a hetero-polysaccharide composed of alternating residues of D-glucuronic acid and N-acetyl-D-glucosamine. It is a straight-chained polymer with a molecular weight in the range of 50,000 to $13 \times 10^6$ Da, according to the source from which it is obtained and the methods used to prepare it.

It is present in nature in the pericellular gels, the fundamental substance of the connective tissue in vertebrate organisms (of which it represents one of the chief components), in the synovial fluid of joints, in the vitreous humor and umbilical cord.

HA therefore plays an important role in the biological organism (besides those described above), as a mechanical support for the cells of many tissues, such as the skin, tendons, muscles and cartilage.

Said polysaccharide is known to be used as a vehicle for drugs of various kinds, in simple associations or salified with hyaluronic acid, since its special properties of biocompatibility, biodegradability, non-immunogenicity, viscosity and hydratability make it particularly suitable as a release system for drugs and molecules both at a topical and systemic level (EP0197718B1, EP0445255B1).

Indeed, preclinical experiments with HA associated with anti-inflammatories (such as Diclofenac) for topical use have demonstrated that HA significantly increases (compared to controls) absorption of the drug into the skin where, thanks to the specific action of hyaluronic acid, it is compartmented to form a "reservoir", minimising further absorption through the skin. The drug's action (and efficacy) is thus significantly increased (Brown M. B. et al., JEADV, 2005, 19:309-318).

The Applicant, contrary to the above description of HA as a delivery system, has surprisingly discovered that an association between HA and/or the derivatives thereof with the enzyme collagenase determines a clear reduction in the enzyme's activity, thus enabling the degradation/removal of the eschar with simultaneous formation of granulation tissue, thanks to the specific action of HA.

Moreover, said polysaccharide protects the healthy tissue surrounding the lesion from the digestive action of collagenase, thus increasing patient compliance with the product.

By slowing down the proteolytic activity of collagenase, hyaluronic acid manifests properties that prove to be the absolute opposite of those of the delivery system described above, as known to an expert in the current state of the art.

A further subject of the present invention is represented by pharmaceutical formulations of a lipophilic nature, containing collagenase in association with HA, that enable the complete stabilisation of the enzyme and, therefore, its maintenance in an active form, at room temperature for prolonged periods of time.

DETAILED DESCRIPTION OF THE INVENTION

The present invention describes and claims the association of HA and/or the derivatives thereof with the enzyme collagenase in pharmaceutical formulations of a lipophilic nature which, thanks to the presence of special excipients/stabilisers, allow the proteolytic enzyme to remain stable at room temperature for prolonged periods of time.

Thanks to HA's special properties in tissue regeneration, enzymatic débridement by the new enzyme/HA composition substantially modifies the phases of eschar removal and new tissue regeneration that normally follow treatment with collagenase alone, permitting the establishment of new phases that determine proper wound healing without the formation of pathological scarring:
- the degradation/removal of eschar occurs at the same time as the formation of granulation tissue;
- the formation of new connective tissue determines a reduction in wound size after eschar removal (for the reasons given above) and, hence, a significant decrease in the risk of bacterial and/or viral infections;
- the healthy surrounding tissue is protected from the digestive action of collagenase thanks to HA;
- eschar removal can be performed painlessly.

The claims of the new collagenase/HA formulations described above are possible because HA has proved capable of modulating the proteolytic activity of collagenase significantly slowing down its action during enzymatic débridement of the necrotic tissue, as demonstrated hereafter.

The formulation of enzyme/HA is particularly indicated in the débridement of burns of varying depth, pressure sores, vascular ulcers and diabetic foot ulcers, wounds of various nature and of different sizes and depth and, moreover, in the treatment of hypertrophic and keloid scars with final patient compliance with the product that is decidedly greater than that with the enzyme alone.

Furthermore, said composition is also claimed in the treatment of Dupuytren's contracture and glaucoma.

The HA derivatives that can be used in the new formulations that are the subject of the present invention are listed below:

1. HA salified with organic and/or inorganic bases with a molecular weight of 50-730 KDa (EP0138572 B1) or with a high molecular weight of 750-1230 KDa, (EP 535200 B1);
2. Hyaff®: esters of HA with alcohols of the aliphatic, araliphatic, cycloaliphatic, aromatic, cyclic or heterocyclic series, with a percentage of esterification that may vary according to the type and length of the alcohol used, between 1 and 100%, preferably between 50 and 75% (EP 216453 B1);
3. Hyadd™: amides of HA with amines of the aliphatic, araliphatic, cycloaliphatic, aromatic, cyclic and heterocyclic series, with a percentage of amidation of between 1 and 10%, preferably 4% (EP 1095064 B1);
4. O-sulphatated derivatives of HA up to the 4th degree of sulphatation (EP 0702699 B1);
5. ACP®: inner esters of HA with a percentage of inner esterification between 0.5 and 10% and preferably 5% (EP 0341745 B1);
6. Deacetylated HA derivatives: derived from the deacetylation of the N-acetyl-glucosamine fraction with a percentage of deacetylation preferably between 0.1 and 30%, while all the carboxy groups of HA can be salified with organic and/or inorganic bases (EP1313772 B1);
7. Hyoxx™: percarboxylated derivatives of HA obtained from the oxidation of the primary hydroxyl of the N-acetyl-glucosamine fraction with a degree of percarboxylation of between 0.1 and 100% and preferably between 25 and 75%. All the carboxy groups of HA can be salified with organic and/or inorganic bases (patent application No. EP1339753).

The HA used in the present invention as such or in the preparation of its derivatives may be derived from any source, for example it may be obtained by extraction from rooster combs (EP0138572 B1), by fermentation, or by technological means and its molecular weight may vary between 400 and $3 \times 10^6$ Da, in particular between $1 \times 10^5$ Da and $1 \times 10^6$ Da, and more particularly still between 50,000 and 200,000 Da.

The concentration of the collagenase enzyme to be used in association with HA or the derivatives thereof may vary between 0.01 U and 100 U/milligram of HA, preferably between 0.1 and 20 U and more preferably still between 0.2 and 10 U/mg of HA.

The final concentration of HA or the derivatives thereof in the final pharmaceutical composition may vary between 0.01 and 5% weight/weight of the final product, ranging preferably between 0.1 and 2% w/w, and more preferably still between 0.2 and 0.4% w/w.

One unit of collagenase is defined as the quantity of enzyme that hydrolyses 1 nmole of PZ-Pro-Leu-Gly-Pro-D-Arg in one second at pH equal to 7.1 and at 37° C. (PZ=4-phenyl-azobenzyloxycarbonyl) (Wunsch E. et al, Physiol Chem, 1963, 333:149-151).

The collagenase preferably used or to be used in the compositions that are the subject of the present invention is that produced from the non-pathogenic micro-organism belonging to the *Vibrio Alginolyticus* sub. *Iophagus* strain, NCIMB (National Collection of Industrial and Marine Bacteria), strain number 11038, equivalent strain: LMG 3418.

It is a gram negative micro-organism that produces a collagenase with a molecular weight of from 90,000 to 110,000 Daltons, (IUBMB nomenclature: EC 3.4.24.3), stable in a pH range of 4.0 and 11.0 but with an optimal pH of between 6.0 and 8.0, stable at temperatures varying between 4 and 40° C. with an optimal temperature of 37° C.

The enzyme is defined as a metalloendopeptidase because it breaks up the collagen into peptide fragments, acting directly on its triple-chain protein structure. The specific activity of the enzyme is inhibited by the silver and copper salts and also by chelating agents such as EDTA, which bind the calcium ion necessary to collagenase activity.

Collagenolytic Activity of Collagenase from *Vibrio Alginolyticus* Versus the Activity of the Same Enzyme Associated with Hyaluronic Acid The aim of the study was to compare the activity of the enzyme as such with that of the new composition of collagenase/HA, to observe the influence of hyaluronic acid on the proteolytic activity of the same enzyme.

Material:
collagen extracted from bovine skin at a concentration of 1 mg/ml (of buffer prepared as described hereafter) as a substrate for enzymatic activity;
collagenase extracted from *Vibrio Alginolyticus* tested at three different concentrations of 0.33, 0.66 and 1.32 enzyme units;
collagenase extracted from *Vibrio Alginolyticus* tested at the same three concentrations of 0.33, 0.66 and 1.32 U but in association with hyaluronic acid at the following ratios: 0.16 U/mg of HA, 0.33 U or 0.66 U/mg of HA (hence, 0.33, 0.66 and 1.32 U are associated with 2 mg of HA). In all three cases, the concentration of the polysaccharide was kept constant.

Method of Enzymatic Digestion:
the collagen degradation process was performed at 37° C. for a time period initially set at 90 minutes. Subsequently, the process was repeated at the same concentrations and at the same temperature, but the reaction was halted 4 and 12 hours after it was begun.

The digestion reaction occurred in Tris-HCL buffer, 0.05 M, containing $CaCl_2$ 0.01M at pH=7.4 to which the reaction substrate had been added, either collagenase itself or the enzyme associated with set concentrations of HA as described above.

Results:
the enzymatic digestion mixture obtained (enzyme and relative collagen degradation products) was analysed on 7% polyacrylamide gel (electrophoresis: SDS-PAGE; Laemmli U. K., Nature, 1970, 680-685), to map the various protein fragments separated according to their molecular weight, (MW) and stained with Comassie blue.

After the electrophoresis run, the collagen separates into subunits with a MW of about 100,000 Daltons with further peptide fragments with a MW of about 33,000 Daltons.

All the gels were loaded with molecular weight standards, with undigested collagen as positive control, with collagen degraded by collagenase as such and relative enzyme separately loaded and, lastly, with collagen degraded by collagenase associated with HA and enzyme alone.

Figure 1:
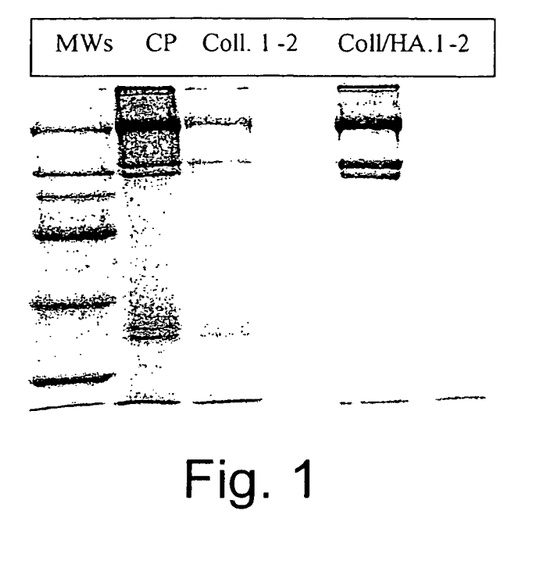
FIG. 1: Collagen digestion time of 90 minutes
MWS=molecular weight standards represented by 6 bands: 205 KDs, 116 KDs, 97 KDs, 66 KDs, 45 KDs, 29 KDs; CP=Collagen as such, Positive control; Coll. 1=Collagenase at a concentration of 0.33 U+collagen; Coll. 2=Collagenase at a concentration of 0.33 U; Coll./HA 1=Collagenase at a concentration of 0.33 U+collagen in the presence of HA; Coll./HA 2=Collagenase at a concentration of 0.33 U in the presence of HA.

FIG. 1 clearly shows that 0.33 U enzymes only partially degrade collagen in 90 minutes but, above all, that the presence of HA in the collagenase/HA composition (at the same concentration of enzyme) modifies the collagenolytic action of the enzyme, reducing its activity.

Figure 2:
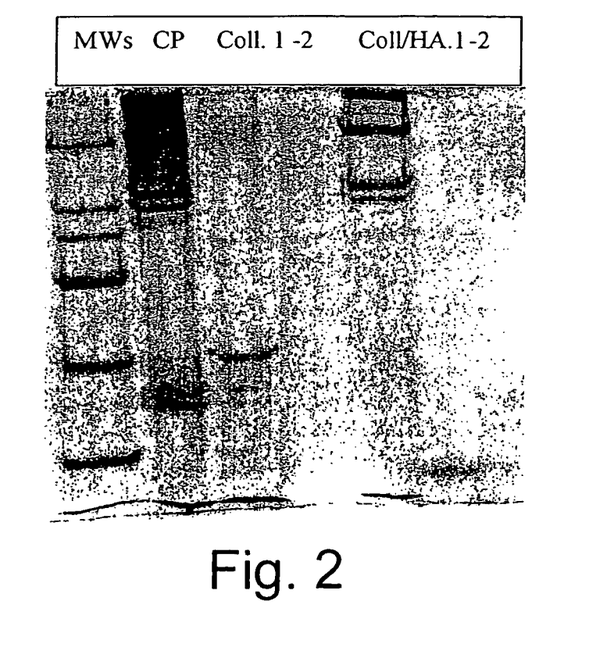
FIG. 2: Collagen digestion time of 90 minutes
MWS=molecular weight standards represented by 6 bands: 205 KDs, 116 KDs, 97 KDs, 66 KDs, 45 KDs, 29 KDs; CP=Collagen as such, Positive control; Coll. 1=Collagenase at a concentration of 0.66 U+collagen; Coll. 2=Collagenase at a concentration of 0.66 U; Coll./HA 1=Collagenase at a concentration of 0.66 U+collagen in the presence of HA; Coll./HA 2=Collagenase at a concentration of 0.66 U in the presence of HA.
Figure 3:
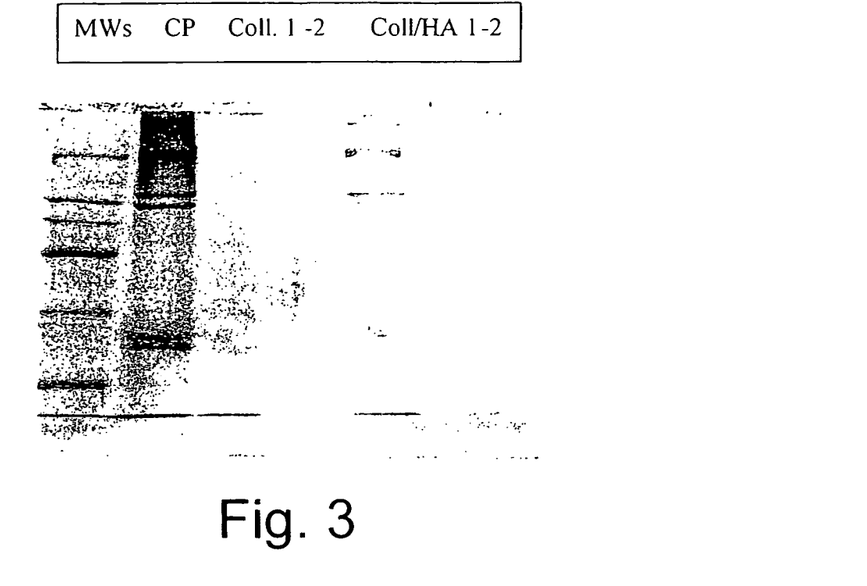
FIG. 3: Collagen digestion time of 90 minutes
MWS=molecular weight standards represented by 6 bands: 205 KDs, 116 KDs, 97 KDs, 66 KDs, 45 KDs, 29 KDs; CP=Collagen as such, Positive control; Coll. 1=Collagenase at a concentration of 1.32 U+collagen; Coll. 2=Collagenase at a concentration of 1.32 U; Coll./HA 1=Collagenase at a concentration of 1.32 U+collagen in the presence of HA; Coll./HA 2=Collagenase at a concentration of 1.32 U in the presence of HA.

FIGS. 2 and 3 further show the modulatory action exercised by hyaluronic acid on the enzyme: after 90 minutes 0.66 and 1.32 U of collagenase completely degrade the collagen while, especially at 0.66 U, HA slows down the collagenolytic action of the enzyme. The influence of said polysaccharide on the enzyme is even more evident with 1.32 U of collagenase.

Figure 4:
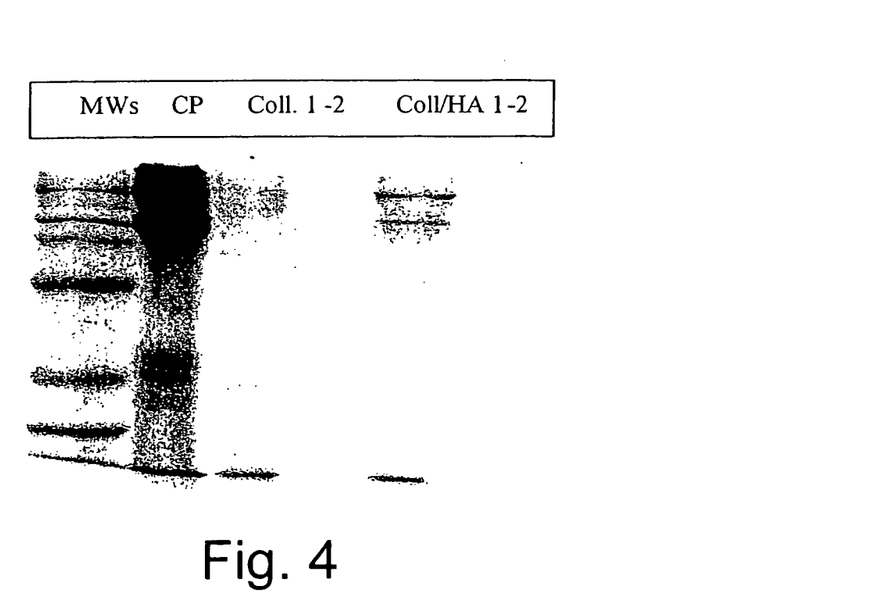
FIG. 4: Collagen digestion time of 4 hours
MWS=molecular weight standards represented by 6 bands: 205 KDs, 116 KDs, 97 KDs, 66 KDs, 45 KDs, 29 KDs; CP=Collagen as such, Positive control; Coll. 1=Collagenase at a concentration of 0.66 U+collagen; Coll. 2=Collagenase at a concentration of 0.66 U; Coll./HA 1=Collagenase at a concentration of 0.66 U+collagen in the presence of HA; Coll./HA 2=Collagenase at a concentration of 0.66 U in the presence of HA
Figure 5:
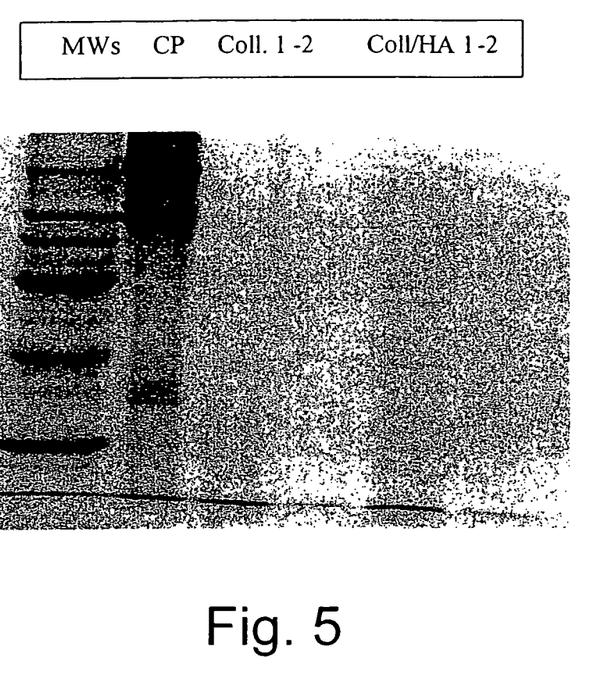
FIG. 5: Collagen digestion time of 12 hours
MWS=molecular weight standards represented by 6 bands: 205 KDs, 116 KDs, 97 KDs, 66 KDs, 45 KDs, 29 KDs; CP=Collagen as such, Positive control; Coll. 1=Collagenase at a concentration of 0.66 U+collagen; Coll. 2=Collagenase at a concentration of 0.66 U; Coll./HA 1=Collagenase at a concentration of 0.66 U+collagen in the presence of HA; Coll./HA 2=Collagenase at a concentration of 0.66 U in the presence of HA.

FIGS. 4 and 5 show the situation after 4 and 12 hours: after 4 hours of incubation of the enzyme (0.66 U) with collagen it is still possible to observe the action of HA on collagenase because the undigested protein fractions of collagen are visible, albeit faintly; after 12 hours (again with 0.66 U of enzyme) the modulatory action of the polysaccharide is no longer evident and the collagen is completely degraded.

For purely descriptive purposes, and without being limited by the same, we report hereafter some examples of how the new formulations that are the subject of the present invention can be prepared:

Method of Producing Collagenase/HA Lipogel
Preparation of the Functional Components of the Lipogel:
An initial aqueous solution or a buffer solution at pH 7.1 (TrisHCL 25 mM, $CaCl_2$ 10 mM) is prepared with 82.7 U/ml of collagenase; 45 ml of this solution is freeze-dried with the following excipients: Maltose (18 g) as diluent/stabiliser, Carrageenan, possibly purified (0.54 g) as stabiliser and water 45 g. 18.6 g of freeze-dried product is obtained (dry product), composed as follows:
maltose 95% w/w
carrageenan 2.8% w/w
collagenase 0.9% w/w
The freeze-dried product is then micronised.
At the same time, HA obtained by fermentation and with a MW of 160 KDs is also micronised.

Dispersion of the Functional Components in the Lipophilic Base:

Examples 1 and 2

The enzyme collagenase and HA prepared as described above are evenly dispersed in a lipophilic base constituted by the following excipients:
hydrogenated castor oil in powder form (with gelling action)
cetylstearylic alcohol (as agent of consistence)
stringy Vaseline (as lipophilic phase)
light Vaseline oil (as lipophilic phase)

Preparation of the Lipophilic Base:
dissolve and solubilise at about 88-90° C. the stringy Vaseline and cetylstearylic alcohol in the Vaseline oil. Once a smooth, melted mass has been obtained, dissolve and solubilise the hydrogenated castor oil powder in the newly formed lipophilic phase.

Once the mass is evenly melted, cool to 25-30° C.

| | Function | % w/w (weight/weight) |
|---|---|---|
| Main components | | |
| Micronised HA | | 0.2 |
| Freeze-dried, micronised collagenase | | 1.8 U/g |

|  | Function | % w/w (weight/weight) |
|---|---|---|
| Excipients | | |
| Hydrogenated castor oil | Gelling agent | 1.0 |
| Cetylstearylic alcohol | Agent of consistence | 5.0 |
| Stringy Vaseline | Lipophilic phase | 36.5 |
| Light Vaseline oil | Lipophilic phase | Q b a 100 |

|  | Function | % w/w (weight/weight) |
|---|---|---|
| Main components | | |
| Micronised HA | | 0.2 |
| Freeze-dried, micronised collagenase | | 1.5 U/g |
| Excipients | | |
| Hydrogenated castor oil | Gelling agent | 1.0 |
| Cetylstearylic alcohol | agent of consistence | 5.0 |
| Stringy Vaseline | Lipophilic phase | 36.5 |
| Light Vaseline oil | Lipophilic phase | Q b a 100 |

|  | Function | % w/w (weight/weight) |
|---|---|---|
| Main components | | |
| Micronised HA | | 1 |
| Freeze-dried, micronised collagenase | | 1.8 U/g |
| Excipients | | |
| Hydrogenated castor oil | Gelling agent | 1.0 |
| Cetylstearylic alcohol | agent of consistence | 5.0 |
| Stringy Vaseline | Lipophilic phase | 36.5 |
| Light Vaseline oil | Lipophilic phase | Q b a 100 |

|  | Function | % w/w (weight/weight) |
|---|---|---|
| Main components | | |
| Micronised HYAFF (50% esterified with benzyl alcohol) | | 0.2 |
| Freeze-dried, micronised collagenase | | 1.8 U/g |
| Excipients | | |
| Hydrogenated castor oil | Gelling agent | 1.0 |
| Cetylstearylic alcohol | agent of consistence | 5.0 |
| Stringy Vaseline | Lipophilic phase | 36.5 |
| Light Vaseline oil | Lipophilic phase | Q b a 100 |

|  | Function | % w/w (weight/weight) |
|---|---|---|
| Main component | | |
| Micronised HA | | 0.2 |
| Freeze-dried, micronised collagenase | | 1.8 U/g |
| Excipients | | |
| Hydrogenated castor oil | Gelling agent | 1.0 |
| Cetylstearylic alcohol | agent of consistence | 10.0 |
| Stringy Vaseline | Lipophilic phase | 34.5 |
| Light Vaseline oil | Lipophilic phase | Q b a 100 |

|  | Function | % w/w |
|---|---|---|
| Main component | | |
| Micronised HA | | 0.2 |
| Freeze-dried, micronised collagenase | | 2 U/g |
| Excipients | | |
| Hydrogenated castor oil | Gelling agent | 1.0 |
| Cetylstearylic alcohol | agent of consistence | 10.0 |
| Stringy Vaseline | Lipophilic phase | 34.5 |
| Light Vaseline oil | Lipophilic phase | Q b a 100 |

Dispersion of the Functional Components in the Lipophilic Base:

Example 3

Incorporate and solubilise light Vaseline oil in Jojoba Glaze while slowly stirring at 70-75° C. (lipophilic gelling system based on styrene copolymers-propylene-butylene in Jojoba oil) until a smooth mass is obtained. Cool to room temperature and then add, while stirring, Micronised HA and micronised, lipophilic Collagenase as previously described, until the powders have been completely amalgamated in the lipogel.

|  | Function | % w/w |
|---|---|---|
| Main component | | |
| Micronised HA | | 0.2 |
| Accessory component | | |
| Freeze-dried, micronised collagenase | | 1.8 U/g |

| | Function | % w/w |
|---|---|---|
| Excipients | | |
| Jojoba Glaze LV | Lipophilic phase viscous agent | 80.0 |
| Light Vaseline oil | Lipophilic phase | Q.s a 100 |

| | Function | % w/w |
|---|---|---|
| Main component | | |
| Micronised HA | | 0.2 |
| Accessory component | | |
| Freeze-dried, micronised collagenase | | 1.5 U/g |
| Excipients | | |
| Jojoba Glaze LV | Lipophilic phase viscous agent | 80.0 |
| Light Vaseline oil | Lipophilic phase | Q.s a 100 |

Said formulations may contain pharmacologically and/or biologically active substances such as, for example, antibiotics, antivirals, wound healers, cytostatic/cytotoxic agents, anticancer drugs, hormones, steroid and non-steroid anti-inflammatory drugs, trophic factors and cytokines of various nature.

The invention being thus described, it is clear that these methods can be modified in various ways. Such modifications are not to be considered as divergences from the spirit and purpose of the invention and any modification that would be evident to an expert in the field comes within the scope of the following claims.

The invention claimed is:

1. A method for treating burns of varying depth, pressure sores, vascular ulcers or diabetic foot ulcers, and wounds by the enzymatic debridement for eschar removal which comprises administering a pharmaceutical composition comprising hyaluronic acid or at least one hyaluronic acid derivative and the proteolytic enzyme collagenase, wherein said collagenase is from the non-pathogenic micro-organism belonging to the strain *Vibrio Alginolyticus* sub. *Iophagus*, said hyaluronic acid derivative is at least one member selected from the group consisting of salts of hyaluronic acid with organic and/or inorganic bases, amides, sulphatated derivatives, deacetylated derivatives and percarboxylated derivatives, the concentration of the proteolytic enzyme collagenase is between 0.01 U and 100 U/milligrams of said hyaluronic acid or said hyaluronic acid derivative, said hyaluronic acid or said hyaluronic acid derivative is present in a concentration of between 0.01 and 5% weight/weight of the composition and wherein said hyaluronic acid or the hyaluronic acid used in the preparation of said at least one hyaluronic acid derivative has a molecular weight of between 50 kDa and 200 kDa.

2. The method according to claim 1, wherein said pharmaceutical composition further comprises an additional pharmacologically and/or biologically active substance.

3. The method according to claim 1, wherein the concentration of the enzyme collagenase ranges between 0.1 and 20 U/milligrams of said hyaluronic acid or of said hyaluronic acid derivative.

4. The method according to claim 3, wherein the concentration of the enzyme collagenase is between 0.2 and 10 U/milligrams of said hyaluronic acid or of said hyaluronic acid derivative.

5. The method according to claim 1, wherein the concentration of said hyaluronic acid or of said hyaluronic acid derivative is between 0.1 and 2% w/w.

6. The method according to claim 5, wherein the concentration of said hyaluronic acid or of said hyaluronic acid derivative is between 0.2 and 0.4% w/w.

7. A method for treating burns of varying depth, pressure sores, vascular ulcers, diabetic foot ulcers, and wounds by enzymatic debridement for eschar removal which comprises administering a pharmaceutical composition comprising (a) hyaluronic acid or at least one hyaluronic acid derivative, (b) the proteolytic enzyme collagenase, and (c) maltose and carrageenan as stabilizing agents, wherein said collagenase is from the non-pathogenic micro-organism belonging to the strain *Vibrio Alginolyticus* sub. *Iophagus*, said hyaluronic acid derivative is at least one member selected from the group consisting of salts of hyaluronic acid with organic and/or inorganic bases, amides, sulphatated derivatives, deacetylated derivatives and percarboxylated derivatives, the concentration of the proteolytic enzyme collagenase is between 0.01 U and 100 U/milligrams of said hyaluronic acid or said hyaluronic acid derivative, said hyaluronic acid or said hyaluronic acid derivative is present in a concentration of between 0.01 and 5% weight/weight of the composition and wherein said hyaluronic acid or the hyaluronic acid used in the preparation of said at least one hyaluronic acid derivative has a molecular weight of between 50 kDa and 200 kDa.

8. A method for treating burns of varying depth, pressure sores, vascular ulcers, diabetic foot ulcers, and wounds by enzymatic debridement for eschar removal which comprises administering a pharmaceutical composition comprising (a) hyaluronic acid or at least one hyaluronic acid derivative, (b) the proteolytic enzyme collagenase, and (c) maltose and carrageenan as stabilizing agents, wherein said collagenase is from the non-pathogenic micro-organism belonging to the strain *Vibrio Alginolyticus* sub. *Iophagus* said hyaluronic acid derivative is at least one member selected from the group consisting of salts of hyaluronic acid with organic and/or inorganic bases, amides, sulphatated derivatives, deacetylated derivatives and percarboxylated derivatives, the concentration of the proteolytic enzyme collagenase is between 0.02 U and 20 U/milligrams of said hyaluronic acid or said hyaluronic acid derivative, said hyaluronic acid or said hyaluronic acid derivative is present in a concentration of between 0.01 and 5% weight/weight of the composition and wherein said hyaluronic acid or the hyaluronic acid used in the preparation of said at least one hyaluronic acid derivative has a molecular weight of between 50 kDa and 200 kDa.

* * * * *

UNITED STATES PATENT AND TRADEMARK OFFICE
CERTIFICATE OF CORRECTION

PATENT NO. : 8,900,576 B2  
APPLICATION NO. : 11/921835  
DATED : December 2, 2014  
INVENTOR(S) : Susanna Vaccaro et al.

Page 1 of 1

It is certified that error appears in the above-identified patent and that said Letters Patent is hereby corrected as shown below:

ON THE TITLE PAGE:

At item (73), Assignee, change "Fidia Farmaceutici S.p.A., Padua (IT)" to --Fidia Farmaceutici S.p.A., Abano Terme (IT)--.

Signed and Sealed this  
Twentieth Day of October, 2015

Michelle K. Lee  
*Director of the United States Patent and Trademark Office*